June 11, 1946. R. G. JELLY Plant Pat. 695
ROSE PLANT
Filed Nov. 21, 1945
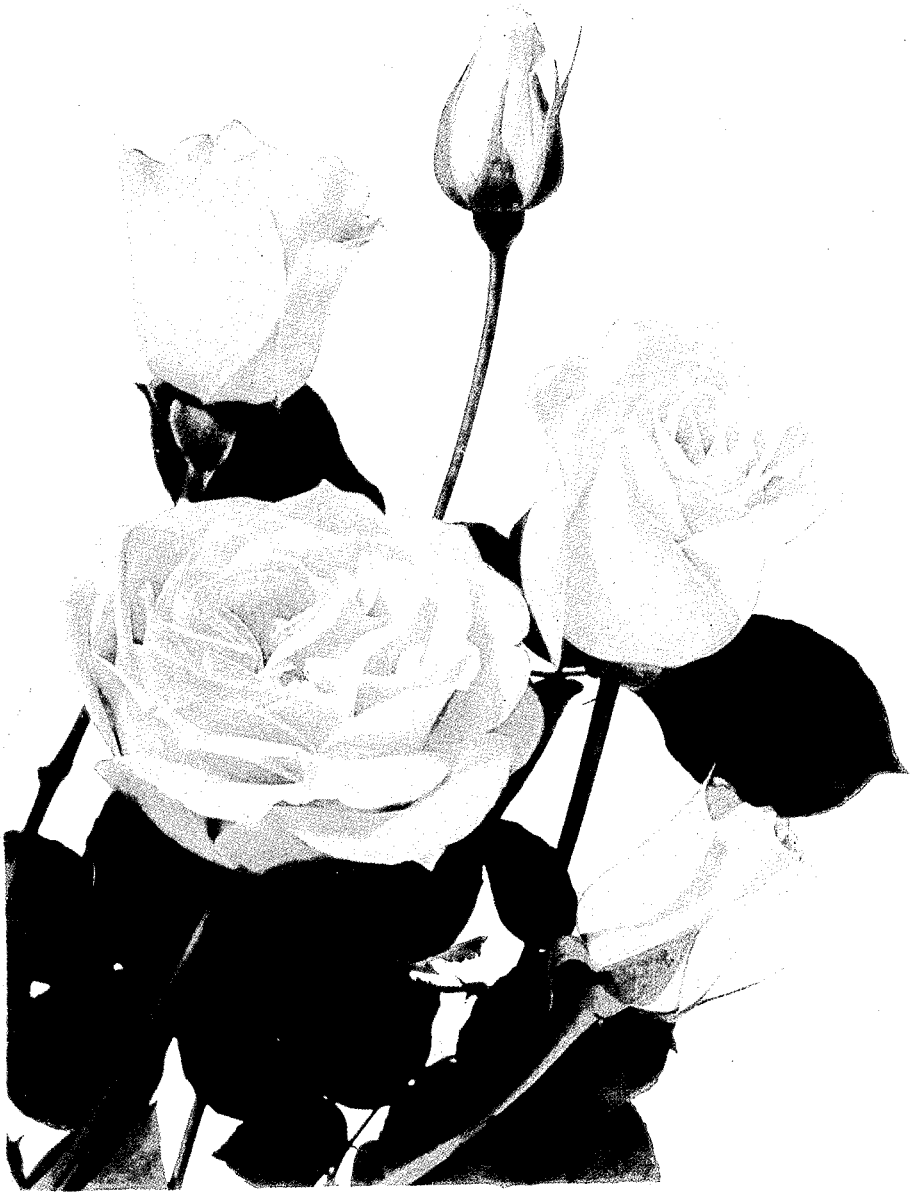
Inventor
R. G. Jelly
By Robb & Robb
His attorneys Patented June 11, 1946 Plant Pat. 695

UNITED STATES PATENT OFFICE

695

ROSE PLANT

Robert G. Jelly, Richmond, Ind., assignor to The E. G. Hill Company, Richmond, Ind., a corporation of Indiana Application November 21, 1945, Serial No. 629,999½

1 Claim. (Cl. 47—61)

The present invention relates to a new and distinct variety of hybrid tea rose plant, originated by the crossing of two well-known varieties "Golden Rapture" (Geheimrat Duisberg) and "Carmelita" (Plant Patent No. 91).

This new variety is completely distinct from any known rose in commerce, including its parent varieties. Among the distinguishing characteristics is its free growing habit in the greenhouse, producing a high percentage of perfect flowers borne on medium length stems.

The foliage is of good color as hereinafter specified and shown in the accompanying illustration, and is resistant to mildew and blackspot infection.

The flower is very spicy in fragrance, and in color and form can best be compared to the variety "Queen Mary" (Plant Patent No. 249), in that it carries the shadings and colorings of that variety. The stems in the present variety, however, are not as long as those of "Queen Mary," but it produces many more flowers.

Taking all of the distinctive features of this new rose into consideration, it may be stated that, from a commercial standpoint, it has all the characteristics of a rose that are necessary for a good forcing variety.

Asexual reproduction of this new rose variety shows the foregoing characteristics come true to form and are established.

The following is a detailed description of the new variety, color terminology being in accord with Ridgway's Color Standard, except where otherwise indicated by ordinary dictionary definition:

Type: Bush; greenhouse; seedling; for cut flowers.
Class: Hybrid tea.
Discovery: At Richmond, Indiana.
*Seedling.*—Seed parent—"Golden Rapture." Pollen parent—"Carmelita."
Propagation: Holds its distinguishing characteristics through succeeding propagations by cuttings, grafting, and budding.

*Flower*

Locality where grown: Richmond, Indiana.
Flowers borne: Singly; on strong, medium length stems.
Quantity of bloom: Free, in greenhouse.
Continuity: Continuous.
Fragrance: Strong; spicy.
Bud:
*Peduncle.*—Short; heavy; stiff; medium green; entirely smooth.
*Before calyx breaks.—Size*—medium large. *Form*—pointed; without foliaceous appendages on the surface of the bud; without foliaceous parts extending beyond the tip of the bud.

*As calyx breaks.—Color*—margin of petal deep shade Rose Doree overlaid with scarlet. Yellow suffusion from base well up into petal.
*As first petal opens.—Size*—2 inches by 2 inches.
*Opening.*—Opens up well.
Bloom:
*Size.*—When fully open, large; 6 to 7 inches.
*Petalage.*—Double; stamens apparent in open flower; 30 to 35 petals; arranged regularly.
*Form.*—High center, becoming flat; petals remaining at first very tightly rolled outward; becoming later, at maturity, flat cupped, rolled outward.
Petals: Thick; with inside and outside shiny.
*Shape.*—Outside—round, obovate. Intermediate—obovate. Inside—obovate.
*Color.*—Geranium Pink shaded with yellow at the base.

This description of a newly opened flower was made from a rose grown in a greenhouse in the month of May, 1945, at Richmond, Indiana, during a cloudy period:

*Color.—Outside petal*—outside surface: Geranium Pink, Yellow base, Plate XII; inside surface: Geranium Pink, Yellow base, Plate XII. *Intermediate petal*—outside surface: Geranium Pink, Yellow base, Plate XII; inside surface: Geranium Pink, Yellow base, Plate XII. *Inner petal*—outside surface: Geranium Pink, Yellow base, Plate XII; inside surface: Geranium Pink, Yellow base, Plate XII.

This description was made from a rose that was open for three days in a greenhouse in the month of May, 1945, at Richmond, Indiana:

*Color.—Outside petal*—Outside surface: Geranium Pink, Yellow base; inside surface: Geranium Pink, Yellow base. *Inside petal*—outside surface: Geranium Pink, Yellow base; inside surface: Geranium Pink, Yellow base.
*General color effect.*—Newly opened flower—Geranium Pink, Yellow base. Three days open—Geranium Pink, Yellow base.
*Behavior.*—Persist.
*Flower longevity.*—Cut roses grown in greenhouse kept at living-room temperatures, 5 days in May.

*Reproductive organs*

Stamens: Many; arranged regularly about pistils.
Filaments: Medium size; Yellow; most with anthers.
Anthers: Medium large; Yellow; all open at once.
Pollen: Abundant; Gold.
Pistils: Many.

Styles: Even; medium length; medium heavy; bunched.
Stigma: White.
Ovaries: All enclosed in calyx.
Hips: Unobserved.
Sepals: Falling soon; moderately long; curled.
*Color.*—Inside—Veronese Green. Outside—Mineral Green, Plate XVIII.

*Plant*

Foliage:
*Leaves.*—Composed of 5 to 7 leaflets; very abundant; large; very leathery.
*Leaflets.*—*Shape*—Oval, with acute apex; round base, margin simply serrate. *Color*—Mature—upper surface: Dark Green; under surface: Normal Green. Young—upper surface: Dark Bronze; under surface; Moderately Red.
*Rachis.*—Medium heavy; moderately narrow; with moderately short points, turning out at an angle of less than 90°.

*Disease.*—Resistant to mildew and blackspot.
Growth:
*Habit.*—Upright.
*Growth.*—Vigorous.
*Canes.*—Medium heavy.
*Main stem.*—Bright Green. *Thorns*—few; medium length; hooked downward; with short narrow base. *Prickles* — none. *Hairs*—none.
*Branches.*—Bright Green.
*New shoots.*—Bronze.

I claim:

A new and distinct variety of rose plant of the hybrid tea class particularly useful as a forcing variety, characterized as to novelty by its vigorous free growing habit in the greenhouse, producing a high degree of perfect flowers borne on medium length stems; foliage resistant to mildew and blackspot infection; and the coloring and strong spicy fragrance of its flowers, substantially as shown and described.

ROBERT G. JELLY.